United States Patent
Han et al.

(10) Patent No.: US 10,253,674 B2
(45) Date of Patent: Apr. 9, 2019

(54) DEVICE AND METHOD OF PREDICTING NOX GENERATION AMOUNT

(71) Applicants: Hyundai Motor Company, Seoul (KR); Seoul National University R & DB Foundation, Seoul (KR)

(72) Inventors: Kyoungchan Han, Gyeonggi-do (KR); Junyong Lee, Gyeonggi-do (KR); Jun Yu, Gyeonggi-do (KR); Kyoung Min Lee, Gyeonggi-do (KR); Kyoungdoug Min, Seoul (KR); Seungha Lee, Gyeonggi-do (KR); Gyujin Kim, Gyeonggi-do (KR); Youngbok Lee, Incheon (KR)

(73) Assignees: Hyundai Motor Company, Seoul (KR); Seoul National University R & DB Foundation, Seoul (KR)

( * ) Notice: Subject to any disclaimer, the term of this patent is extended or adjusted under 35 U.S.C. 154(b) by 118 days.

(21) Appl. No.: 15/282,949

(22) Filed: Sep. 30, 2016

(65) Prior Publication Data

US 2017/0167350 A1    Jun. 15, 2017

(30) Foreign Application Priority Data

Dec. 10, 2015    (KR) .......................... 10-2015-0176344

(51) Int. Cl.
*F01N 11/00* (2006.01)
*F02D 35/02* (2006.01)
(Continued)

(52) U.S. Cl.
CPC .......... *F01N 11/007* (2013.01); *F02D 35/026* (2013.01); *F02D 41/0235* (2013.01);
(Continued)

(58) Field of Classification Search
CPC .. F02D 35/026; F02D 35/023; F02D 41/0235; F02D 41/1454; F02D 41/1462;
(Continued)

(56) References Cited

U.S. PATENT DOCUMENTS 6,775,623 B2    8/2004    Ali et al.
2007/0255484 A1*    11/2007    Imai .................... F02D 41/0007
                                                                701/102

(Continued)

FOREIGN PATENT DOCUMENTS

JP    2003-328732 A    11/2003
JP    2007-127004 A    5/2007
(Continued)

*Primary Examiner* — Bryan Bui
(74) *Attorney, Agent, or Firm* — Mintz Levin Cohn Ferris Glovsky and Popeo, P.C.; Peter F. Corless

(57) ABSTRACT

A method of predicting NOx generation amount of a compression ignition engine is provided. The method includes predicting a composition ratio of a gas in a mixture and a flame temperature using driving variables of an engine and calculating a nitrogen oxide generation rate using the composition ratio of the gas in the mixture and the flame temperature. Additionally, a nitrogen oxide generation concentration around flame is calculated using the nitrogen oxide generation rate and a total nitrogen oxide generation amount of a cylinder is predicted using the nitrogen oxide generation rate and the nitrogen oxide generation concentration.

10 Claims, 9 Drawing Sheets

(51) Int. Cl.
    *F02D 41/00*         (2006.01)
    *F02D 41/02*         (2006.01)
    *F02D 41/14*         (2006.01)
    *F02D 41/40*         (2006.01)
    *G01N 33/00*        (2006.01)

(52) U.S. Cl.
    CPC ..... *F02D 41/1454* (2013.01); *F02D 41/1462* (2013.01); *F02D 41/403* (2013.01); *G01N 33/0037* (2013.01); *F02D 41/0072* (2013.01); *F02D 41/1458* (2013.01); *F02D 41/402* (2013.01); *F02D 41/405* (2013.01); *F02D 2041/1412* (2013.01); *F02D 2200/0614* (2013.01); *F02D 2200/0618* (2013.01); *F02D 2200/101* (2013.01); *Y02T 10/44* (2013.01)

(58) Field of Classification Search
    CPC .. F02D 41/403; G01N 33/0037; F01N 11/007
    See application file for complete search history.

(56) References Cited

U.S. PATENT DOCUMENTS

| | | | |
|---|---|---|---|
| 2013/0074515 A1* | 3/2013 | Widener | F02C 3/30 |
| | | | 60/780 |
| 2013/0131954 A1* | 5/2013 | Yu | F02D 41/1462 |
| | | | 701/102 |

FOREIGN PATENT DOCUMENTS

| | | |
|---|---|---|
| JP | 2008-184908 A | 8/2008 |
| KR | 10-1234637 B1 | 2/2013 |
| KR | 10-2013-0056706 A | 5/2013 |
| KR | 2013-0056705 A | 5/2013 |

* cited by examiner

DEVICE AND METHOD OF PREDICTING NOX GENERATION AMOUNT

CROSS-REFERENCE TO RELATED APPLICATION

This application claims priority to and the benefit of Korean Patent Application No. 10-2015-0176344 filed in the Korean Intellectual Property Office on Dec. 10, 2015, the entire contents of which are incorporated herein by reference.

BACKGROUND (a) Field of the Invention

The present invention relates to a device and method of predicting NOx generation amount of a compression ignition engine, and more particularly, to a device and method of more accurately predicting NOx generation amount in real time using a combust pressure and driving variables of an engine without additional devices for analyzing exhaust gas or sensors for detecting the NOx amount.

(b) Description of the Related Art

As emission regulations for vehicles having an internal combustion engine becomes stricter, emission during operation of the internal combustion engine is required to be reduced. One developed method for reducing emission includes reduces emission generated in each cylinder of the internal combustion engine during combustion of an air/fuel mixture. Another developed method for reducing emission includes using a post-processing system of an exhaust gas in the internal combustion engine. The post-processing system of the exhaust gas is adapted to convert noxious materials generated at each cylinder during combustion of the air/fuel mixture into harmless materials. For this purpose, catalytic converters are used for converting carbon monoxide, hydrocarbon, and nitrogen oxide into harmless material.

In addition, to efficiently convert noxious materials using the catalytic converters of the exhaust gas, it is necessary to accurately predict the NOx (mono-nitrogen oxides) amount generated in the engine. According to conventional methods and systems, devices for analyzing the exhaust gas or sensors for detecting the NOx amount are used to accurately predict the NOx amount. However, the use of devices for analyzing the exhaust gas or the sensors for detecting the NOx amount causes an increase in overall costs. In addition, compositions in the engine exhaust gas may contaminate the devices for analyzing the exhaust gas or the sensors for detecting the NOx amount thus causing malfunction or failures of the sensors themselves.

Accordingly, a technique for predicting NOx amount has been developed. Reliability, however, may be deteriorated according to the technique due to complex calculation processes and simplified assumptions for simplifying the calculation processes. Additionally, in the conventional arts, since NOx amount is estimated based on the measured value when the engine is in a normal status, an error between a generated amount and a predicted amount may occur due to the deviation between the engines and the deviation of an environmental condition.

The above information disclosed in this section is merely for enhancement of understanding of the background of the invention and therefore it may contain information that does not form the prior art that is already known in this country to a person of ordinary skill in the art.

SUMMARY

The present invention provides a device and method of predicting NOx generation amount of a compression ignition engine having advantages of more accurately predicting NOx amount in real time using a combust pressure and driving variables of an engine without additional devices for analyzing an exhaust gas or sensors for detecting the NOx amount. An exemplary embodiment of the present invention provides a method of predicting NOx generation amount of a compression ignition engine that may include: predicting a composition ratio of a gas in a mixture and a flame temperature using driving variables of an engine; calculating a nitrogen oxide generation rate using the composition ratio of the gas in the mixture and the flame temperature; calculating a nitrogen oxide generation concentration around flame using the nitrogen oxide generation rate; and predicting a total nitrogen oxide generation amount of a cylinder using the nitrogen oxide generation rate and the nitrogen oxide generation concentration.

The driving variables of the engine may include at least one selected from the group consisting of a pilot fuel amount, a pilot injection time, a pilot injection duration, an injected fuel amount, a main injection duration, a main injection time, an engine speed (RPM), an air/fuel ratio (AF), and an exhaust gas recirculation (EGR). The predicting of the composition ratio of the gas may include predicting the composition ratio of the gas of a flame surface of a flame generated by mixing a fuel and an air using the driving variables of the engine. Further, the calculating of the nitrogen oxide generation rate may include deriving the flame temperature of a combustion chamber based on a change in the composition ratio of the gas in the cylinder due to a pilot injection. The calculating of the nitrogen oxide generation rate may further include deriving the nitrogen oxide generation rate using a flame temperature and an oxygen concentration and nitrogen concentration in the combustion chamber. The calculating of the nitrogen oxide generation concentration around the flame may include deriving nitrogen oxide generation time and nitrogen oxide generation area using the fuel amount and the engine speed and calculating the nitrogen oxide generation concentration using the nitrogen oxide generation rate, the nitrogen oxide generation time, and the nitrogen oxide generation area.

The predicting of the total nitrogen oxide generation amount of the cylinder may include calculating nitrogen oxide generation amount around flame using the nitrogen oxide generation rate and the nitrogen oxide generation concentration around the flame, and deriving the total nitrogen oxide generation amount of the cylinder by compensating the nitrogen oxide generation amount around the flame with a concentration of the cylinder. The predicting of the total nitrogen oxide generation amount of the cylinder may further include linearizing the total nitrogen oxide generation amount of the cylinder to a nitrogen oxide predetermined value.

An exemplary embodiment of the present invention provides a device of predicting NOx generation amount of a compression ignition engine that may include: a driving variable collector configured to collect driving variables of an engine; a calculator configured to calculate nitrogen oxide generation rate and nitrogen oxide generation concentration due to a pilot injection using the driving variables of the engine; and a controller configured to predict nitrogen oxide generation amount around flame using the nitrogen oxide generation rate and the nitrogen oxide generation concentration, and predict total nitrogen oxide generation amount of a cylinder from the nitrogen oxide generation amount around the flame.

The calculator may include a nitrogen oxide generation rate calculator configured to predict a composition ratio of a gas in a mixture and a flame temperature using the driving variables of the engine, and predict the nitrogen oxide generation rate using the composition ratio of the gas and the flame temperature. The calculator may further include a nitrogen oxide generation concentration calculator configured to derive nitrogen oxide generation time and nitrogen oxide generation area using a fuel amount and an engine speed, and calculate the nitrogen oxide generation concentration using the nitrogen oxide generation rate, the nitrogen oxide generation time, and the nitrogen oxide generation area.

The controller may include a predictor configured to predict the total nitrogen oxide generation amount of the cylinder from the nitrogen oxide generation amount around the flame. The predictor may include a concentration correction unit configured to derive the total nitrogen oxide generation amount of the cylinder by compensating the nitrogen oxide generation amount around the flame with an entire concentration of the cylinder. The predictor may be configured to linearize the total nitrogen oxide generation amount of the cylinder to a nitrogen oxide predetermined value.

According to the present invention for achieving the object, by calculating the nitrogen oxide generation rate and the nitrogen oxide generation concentration around the flame, predicting the nitrogen oxide generation amount around the flame, and predicting the total nitrogen oxide generation amount of the cylinder from the nitrogen oxide generation amount around the flame, it may be possible to more accurately predict the NOx amount in real time.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

In the following detailed description, only exemplary embodiments of the present invention have been shown and described, simply by way of illustration. As those skilled in the art would realize, the described exemplary embodiments may be modified in various different ways, all without departing from the spirit or scope of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It is understood that the term "vehicle" or "vehicular" or other similar terms as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles, and other alternative fuel vehicles (e.g., fuel derived from resources other than petroleum).

In addition, some methods may be executed by at least one controller. The term "controller" refers to a hardware device including a memory and a processor configured to execute one or more steps interpreted as an algorithm structure. The memory stores algorithm steps, and the processor specifically executes the algorithm steps to perform one or more processes to be described below.

Further, control logic of the present invention may be implemented by a non-transient computer-readable medium on a computer-readable means including executable program instructions executed by a processor, a controller, or the like. Examples of a computer-readable medium, although not restrictive, include ROMs, RAMs, CD-ROMs, magnetic tapes, floppy disks, flash drives, smart cards, and optical data storages. The computer-readable recording medium may be distributed in a network-connected computer system, and for example, may be stored and executed in a distributed manner by a telematics server or Controller Area Network (CAN).

A device and method of predicting NOx generation amount of a compression ignition engine will now be described with reference to FIG. 1 to FIG. 9.

Figure 1:
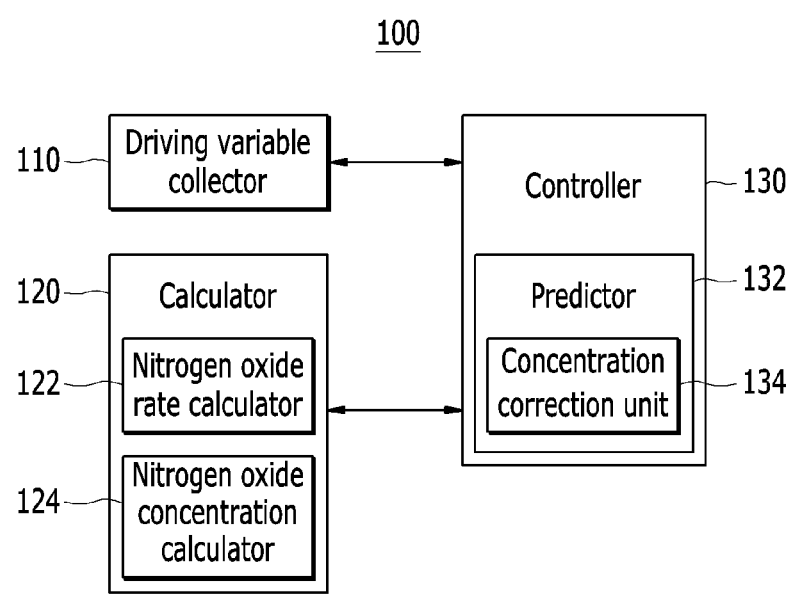
FIG. 1 is a schematic diagram of a device of predicting NOx generation amount according to an exemplary embodiment of the present invention.

FIG. 1 is a schematic diagram of a device of predicting NOx generation amount according to an exemplary embodiment of the present invention. In particular, for convenience of explanation, a configuration of the device of predicting NOx generation amount according to the exemplary embodiment of the present invention is schematically illustrated, but the compression ignition engine is not limited thereto. Referring to FIG. 1, the device of predicting NOx generation amount 100 according to an exemplary embodiment of the present invention may include a driving variable collector 110, a calculator 120, and a controller 130. The controller 130 may be configured to operate the other components of the device (e.g., the driving variable collector 110 and the calculator 120).

Particularly, the driving variable collector 110 may be configured to collect driving variables of the compression ignition engine, and provide or transmit the driving variables of the engine to the controller 130. The driving variables of the engine may include at least one selected from the group consisting of a pilot fuel amount, a pilot injection time, a pilot injection duration, an injected fuel amount, a main injection duration, a main injection time, an engine speed (RPM), an air/fuel ratio (AF), and an EGR. The calculator 120 may be configured to calculate nitrogen oxide generation rate and nitrogen oxide generation concentration around a flame due to a pilot injection using the driving variables of the engine. The calculator 120 may include a nitrogen oxide generation rate calculator 122 and a nitrogen oxide generation concentration calculator 124 according to an exemplary embodiment of the present invention.

The nitrogen oxide generation rate calculator 122 may be configured to predict or determine a composition ratio of the gas in a mixture and a flame temperature using driving variables of the engine, and calculate the nitrogen oxide generation rate around the flame using composition ratio of the gas in the mixture and the flame temperature. The nitrogen oxide generation concentration calculator 124 may be configured to calculate nitrogen oxide generation time and nitrogen oxide generation area using the fuel amount injected to the cylinder and the engine speed (revolutions per minute—RPM). The nitrogen oxide generation concentration calculator 124 may be configured to calculate nitrogen oxide generation concentration around the flame using the nitrogen oxide generation rate, the nitrogen oxide generation time, and the nitrogen oxide generation area. The controller 130 may then be configured to predict or determine nitrogen oxide generation amount around the flame using the nitrogen oxide generation rate and the nitrogen oxide generation concentration around the flame, and predict a total nitrogen oxide generation amount of the cylinder from the nitrogen oxide generation amount around the flame. The controller 130 may include a predictor 132 according to an exemplary embodiment of the present invention.

In particular, the predictor 132 may be configured to predict or determine the total nitrogen oxide generation amount of the cylinder from the nitrogen oxide generation amount around the flame. The predictor 132 may include a concentration correction unit 134 according to an exemplary embodiment of the present invention. The concentration correction unit 134 may be configured to derive the total nitrogen oxide generation amount of the cylinder by compensating the nitrogen oxide generation amount around the flame with the concentration of the cylinder.

Additionally, the predictor 132 may be configured to linearize the total nitrogen oxide generation amount of the cylinder to a nitrogen oxide predetermined value using at least one of nitrogen oxide generation reaction or nitrogen oxide decomposition reaction by nitrogen oxide ($N_2O$). Accordingly, the controller 130 may be implemented with at least one processor operated by a predetermined program, and the predetermined program may be programmed to perform each step according to a method of predicting NOx generation amount according to an exemplary embodiment of the present invention.

Figure 2:
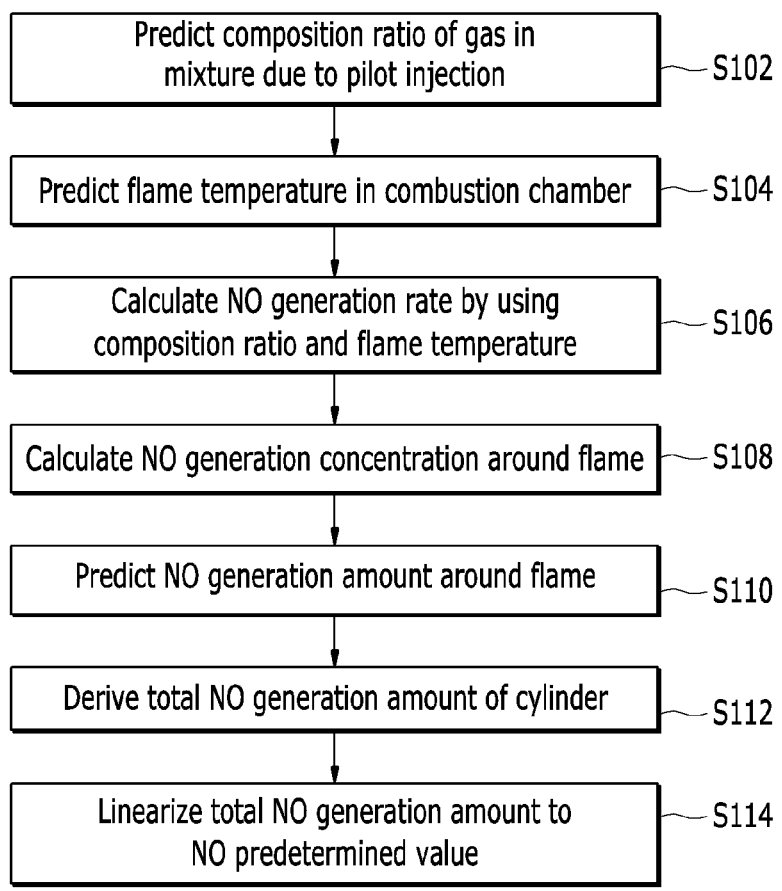
FIG. 2 is a flowchart briefly illustrating a process of predicting NOx generation amount according to an exemplary embodiment of the present invention.
Figure 3:
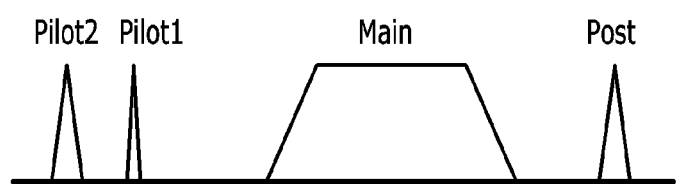
FIG. 3 is a diagram illustrating an example a fuel injection of a compression ignition engine according an exemplary embodiment of the present invention.

Moreover, FIG. 2 is a flowchart briefly illustrating a process of predicting NOx generation amount according to an exemplary embodiment of the present invention. The flowchart will be described with the same reference numerals as that of the configuration of FIG. 1. Referring to FIG. 2, the device of predicting NOx generation amount 100 according to an exemplary embodiment of the present invention may be configured to predict the composition ratio of the gas in the mixture due to the pilot injection at step S102. The device of predicting NOx generation amount 100 may be configured to predict the composition ratio of the gas of the flame surface at which the flame is generated by mixing the fuel with air using the driving variables of the engine FIG. 3 is a diagram illustrating an example a fuel injection of a compression ignition engine according an exemplary embodiment of the present invention. Referring to FIG. 3, in the compression ignition engine according to an exemplary embodiment of the present invention, pilot injection (Pilot1, Pilot2) may be performed before a main injection, and post-injection may be performed after the main injection for reducing a noise and particular matters (PM). In addition, the device of predicting NOx generation amount 100 according to an exemplary embodiment of the present invention may be configured to predict the nitrogen oxide generation amount around the flame by the pilot injection (Pilot1, Pilot2), and predict the total nitrogen oxide generation amount of the cylinder from the nitrogen oxide generation amount around the flame.

The device of predicting NOx generation amount 100 according to an exemplary embodiment of the present invention may be configured to predict the flame temperature in the combustion chamber based on the change of the composition ratio of the gas in the cylinder due to the pilot injection at step S104. The device of predicting NOx generation amount 100 may be configured to calculate the flame temperature in the combustion chamber using the following equation 1.

$$T_{flame} = T_{ad} \times \left(\frac{P_{max}}{P_i}\right)^{\frac{k-1}{k}}$$

wherein, $T_{flame}$ is a flame temperature T, $T_{ad}$ is an adiabatic flame temperature, $P_i$ is pressure of at a start of combustion, $P_{max}$ is a maximum combustion pressure, and K is a specific heat ratio of the combusted gas (burned gas).

The device may further be configured to calculate the nitrogen oxide generation rate using the flame temperature and an oxygen concentration and nitrogen concentration in the combustion chamber at step S106. The nitrogen oxide generation rate may be calculated using the flame temperature T based on a change of the composition ratio of the gas in the mixture due to the pilot injection. Particularly, the nitrogen oxide generation rate in the combustion chamber may be calculated using the following equation 2.

$$\frac{d[NO]}{dt} = \frac{A}{T^{1/2}}\exp\left(\frac{B}{T}\right)[O_2]^{1/2}[N_2] \qquad \text{Equation 2}$$

wherein, $d[NO]/dt$ is the nitrogen oxide generation rate to a time, T is a flame temperature, $[O_2]$ is an oxygen concentration measured by sensor, $[N_2]$ is nitrogen concentration in the combustion chamber, and A and B are constants.

Additionally, the device of predicting NOx generation amount 100 may be configured to calculate the nitrogen oxide generation concentration around the flame using the nitrogen oxide generation rate at step S108. The device may then be configured to derive the nitrogen oxide generation time and the nitrogen oxide generation area using the fuel amount injected to the cylinder and the engine speed. The nitrogen oxide generation concentration around the flame may be calculated using the nitrogen oxide generation rate, the nitrogen oxide generation time, and the nitrogen oxide generation area. In particular, the nitrogen oxide generation concentration around the flame may be calculated using the following equation 3.

$$NO_{mol} = \frac{dNO}{dt} \times S \times T = \frac{dNO}{dt} \times \frac{m_{fuel}}{RPM} \qquad \text{Equation 3}$$

wherein, $NO_{mol}$ is the nitrogen oxide generation concentration around the flame, S is a flame generation area, T is a flame generation duration, $M_{fuel}$ is a fuel amount injected to the cylinder, and RPM is the engine speed The device of predicting NOx generation amount 100 may be configured to predict the nitrogen oxide generation amount around the flame using the nitrogen oxide generation rate around the flame and the nitrogen oxide generation concentration around the flame at step S110. Further, the device of predicting NOx generation amount 100 may be configured to derive the total nitrogen oxide generation amount of the cylinder by compensating the nitrogen oxide generation amount around the flame with the concentration of the cylinder at step S112.

Figure 4:
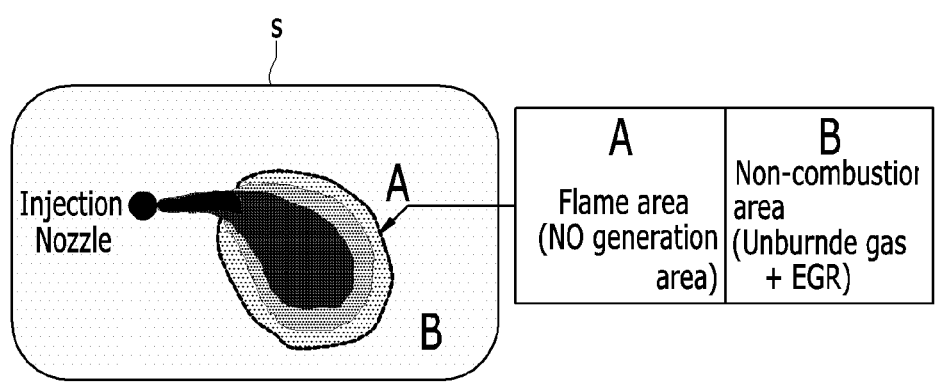
FIG. 4 is a diagram illustrating a flame area according to an exemplary embodiment of the present invention.

FIG. 4 is a diagram illustrating a flame area according to an exemplary embodiment of the present invention. Referring to FIG. 4, in the cylinder S a flame area A may be included in which the flame is generated and a non-combustion area B in which the flame is not generated. The device of predicting NOx generation amount 100 may be configured to derive the nitrogen oxide generation concentration from the flame area A.

Accordingly, the device of predicting NOx generation amount 100 may be configured to calculate the total nitrogen oxide generation amount of the cylinder through a compensation of the concentration based on both the flame area A and the non-combustion area B. In particular, the total nitrogen oxide generation amount of the cylinder may be calculated using the following equation 4.

$$NO = \frac{NO_{mol}}{Volume_A} \times PHI \times \frac{T_A}{T_B} \qquad \text{Equation 4}$$

wherein, nitrogen oxide is the total nitrogen oxide generation amount of the cylinder, $NO_{mol}$ is the nitrogen oxide generation concentration around the flame, $Volume_A$ is a volume of the flame area, PHI is a pressure in the combustion chamber, $T_A$ is the flame temperature in the flame area A, and $T_B$ is a temperature in the non-combustion area B.

The device of predicting NOx generation amount 100 according to an exemplary embodiment of the present invention may be configured to linearize the total nitrogen oxide generation amount of the cylinder to the nitrogen oxide predetermined value at step S114. Additionally, the device may be configured to linearize the total nitrogen oxide generation amount of the cylinder to the nitrogen oxide predetermined value using nitrogen oxide generation reaction by $N_2O$. The following equation 5 denotes the nitrogen oxide generation reaction by $N_2O$ according to an exemplary embodiment of the present invention.

$N_2O+O \Leftrightarrow 2NO$ $O+N_2+M \Leftrightarrow N_2O+M$ $N_2O+H \Leftrightarrow N_2+OH$ $N_2O+O \Leftrightarrow N_2+O_2$ $N_2O+H \Leftrightarrow NO+NH \ldots \Rightarrow 2NO$ \qquad Equation 5

Further, the device of predicting NOx generation amount 100 may be configured to linearize the total nitrogen oxide generation amount of the cylinder to the nitrogen oxide predetermined value based on the nitrogen oxide decomposition reaction which nitrogen oxide is decomposed by the inverse reaction.

Figure 5:
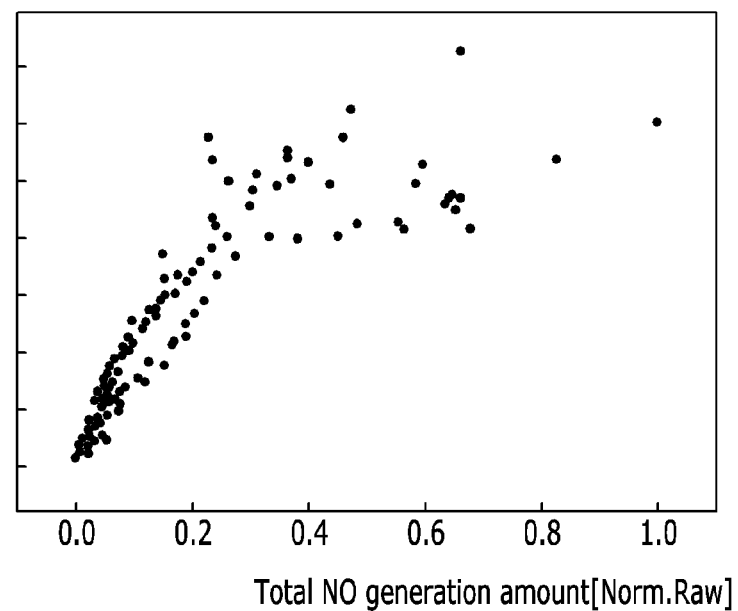
FIG. 5 is a graph illustrating nitrogen oxide generation amount according to the related art.
Figure 6:
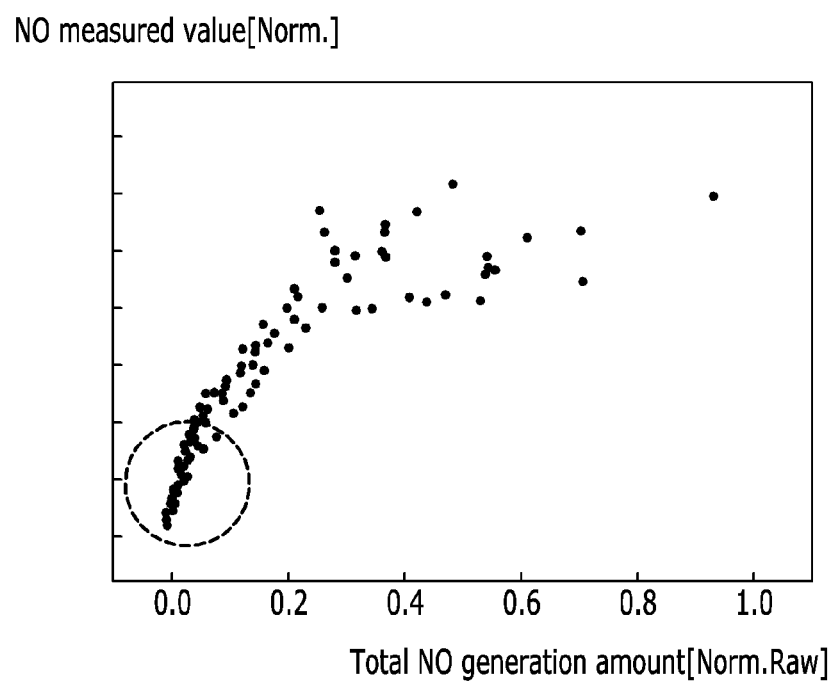
FIG. 6 is a graph illustrating a total nitrogen oxide generation amount of the cylinder predicted using a composition ratio of the gas in a mixture according to an exemplary embodiment of the present invention.
Figure 7:
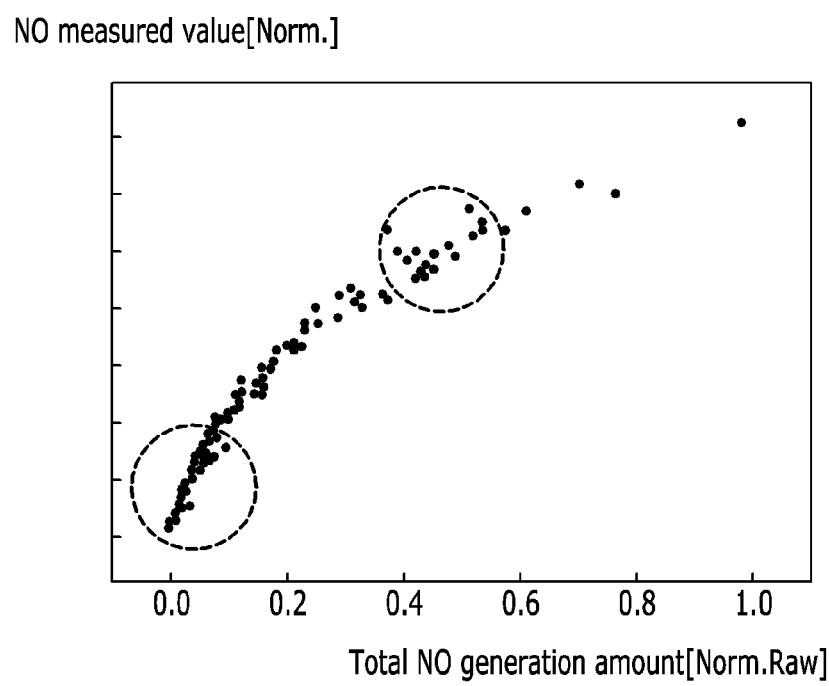
FIG. 7 is a graph illustrating a total nitrogen oxide generation amount of the cylinder predicted using nitrogen oxide generation area in FIG. 6 according to an exemplary embodiment of the present invention.
Figure 8:
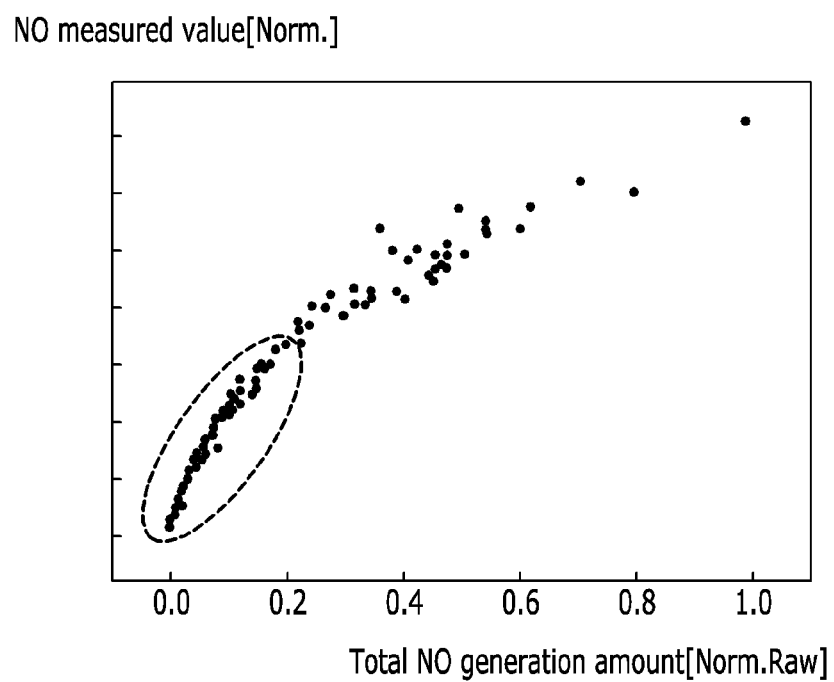
FIG. 8 is a graph illustrating a total nitrogen oxide generation amount of the cylinder predicted using a cylinder entire concentration in FIG. 7 according to an exemplary embodiment of the present invention.
Figure 9:
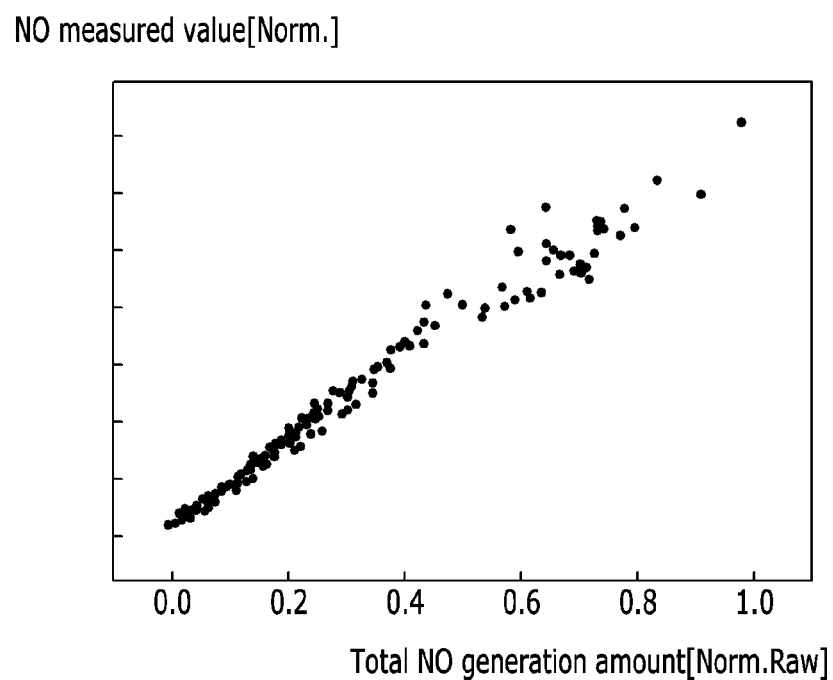
FIG. 9 is a graph illustrating a total nitrogen oxide generation amount of the cylinder predicted using nitrogen oxide decomposition reaction in FIG. 8 according to an exemplary embodiment of the present invention.

FIG. 5 is a graph illustrating nitrogen oxide generation amount according to the related art, and FIG. 6 is a graph illustrating a total nitrogen oxide generation amount of the cylinder predicted using a composition ratio of the gas in a mixture according to an exemplary embodiment of the present invention. FIG. 7 is a graph illustrating a total nitrogen oxide generation amount of the cylinder predicted using nitrogen oxide generation area in FIG. 6, FIG. 8 is a graph illustrating a total nitrogen oxide generation amount of the cylinder predicted using a cylinder entire concentration in FIG. 7, and FIG. 9 is a graph illustrating a total nitrogen oxide generation amount of the cylinder predicted using nitrogen oxide decomposition reaction in FIG. 8.

Referring to FIGS. 6 to 9, in the device of predicting NOx generation amount 100 according to an exemplary embodiment of the present invention, the change of composition ratio of the gas in the mixture due to the pilot injection, the nitrogen oxide generation area, the cylinder entire concentration, and the nitrogen oxide decomposition reaction may be sequentially considered. The device may be configured to linearize the total nitrogen oxide generation amount to the nitrogen oxide measured value which is the nitrogen oxide predetermined value, and the total NOx amount in the cylinder may be more accurately predicted.

As described above, the device and method of predicting NOx generation amount of a compression ignition engine according to an exemplary embodiment of the present invention may be configured to calculate the nitrogen oxide generation rate and the nitrogen oxide generation concentration around the flame, predicts the nitrogen oxide generation amount around the flame, and predicts the total nitrogen oxide generation amount of the cylinder from the nitrogen oxide generation amount around the flame. Therefore, it may be possible to more accurately predict the NOx amount in real time.

The foregoing exemplary embodiments of the present invention are not implemented only by an apparatus and a method, and therefore may be realized by programs realizing functions corresponding to the configuration of the exemplary embodiment of the present invention or recording media on which the programs are recorded.

While this invention has been described in connection with what is presently considered to be exemplary embodiments, it is to be understood that the invention is not limited to the disclosed exemplary embodiments, but, on the contrary, is intended to cover various modifications and equivalent arrangements included within the spirit and scope of the appended claims.

What is claimed is:

1. A method of predicting NOx generation amount of a compression ignition engine, comprising:

predicting, by a controller, a composition ratio of a gas in a mixture and a flame temperature using driving variables of an engine;

calculating, by the controller, a nitrogen oxide generation rate using the composition ratio of the gas in the mixture and the flame temperature;

calculating, by the controller, a nitrogen oxide generation concentration around flame using the nitrogen oxide generation rate; and predicting, by the controller, total nitrogen oxide generation amount of a cylinder using the nitrogen oxide generation rate and the nitrogen oxide generation concentration, wherein the driving variables of the engine includes at least one selected from the group consisting of: a pilot fuel amount, a pilot injection time, a pilot injection duration, an injected fuel amount, a main injection duration, a main injection time, an engine speed (RPM), an air/fuel ratio (AF), and an exhaust gas recirculation (EGR), and wherein the predicting of the total nitrogen oxide generation amount of the cylinder includes calculating, by the controller, the nitrogen oxide generation amount around flame using the nitrogen oxide generation rate and nitrogen oxide generation concentration around the flame, and deriving the total nitrogen oxide generation amount of the cylinder by compensating the nitrogen oxide generation amount around the flame with an entire concentration of the cylinder.

2. The method of claim 1, wherein the predicting of the composition ratio of the gas includes predicting, by the controller, the composition ratio of the gas of a flame surface of a flame generated by mixing a fuel and an air using the driving variables of the engine.

3. The method of claim 2, wherein the calculating of the nitrogen oxide generation rate includes deriving, by the controller, the flame temperature of a combustion chamber based on a change in the composition ratio of the gas in the cylinder due to a pilot injection.

4. The method of claim 3, wherein the calculating of the nitrogen oxide generation rate further includes deriving, by the controller, the nitrogen oxide generation rate using a flame temperature and an oxygen concentration and nitrogen concentration in the combustion chamber.

5. The method of claim 1, wherein the calculating of the nitrogen oxide generation concentration around the flame includes:

deriving, by the controller, a nitrogen oxide generation time and a nitrogen oxide generation area using the injected fuel amount and the engine speed; and calculating, by the controller, the nitrogen oxide generation concentration using the nitrogen oxide generation rate, the nitrogen oxide generation time, and the nitrogen oxide generation area.

6. The method of claim 1, wherein the predicting of the total nitrogen oxide generation amount of the cylinder further includes linearizing, by the controller, the total nitrogen oxide generation amount of the cylinder to a nitrogen oxide predetermined value.

7. A device of predicting NOx generation amount of a compression ignition engine, comprising:

a driving variable collector configured to collect driving variables of an engine;

a calculator configured to calculate a nitrogen oxide generation rate and a nitrogen oxide generation concentration due to a pilot injection using the driving variables of the engine; and a controller configured to predict nitrogen oxide generation amount around flame using the nitrogen oxide generation rate and the nitrogen oxide generation concentration, and predict total nitrogen oxide generation amount of a cylinder from the nitrogen oxide generation amount around the flame, wherein the controller includes a predictor configured to predict the total nitrogen oxide generation amount of the cylinder from the nitrogen oxide generation amount around the flame, and wherein the predictor includes a concentration correction unit configured to derive the total nitrogen oxide generation amount of the cylinder by compensating the nitrogen oxide generation amount around the flame with an entire concentration of the cylinder.

8. The device of claim 7, wherein the calculator includes:

a nitrogen oxide generation rate calculator configured to predict a composition ratio of a gas in a mixture and a flame temperature using the driving variables of the engine, and predict the nitrogen oxide generation rate using the composition ratio of the gas and the flame temperature.

9. The device of claim 8, wherein the calculator includes:

a nitrogen oxide generation concentration calculator configured to derive nitrogen oxide generation time and nitrogen oxide generation area using an injected fuel amount and an engine speed, and calculate the nitrogen oxide generation concentration using the nitrogen oxide generation rate, the nitrogen oxide generation time, and the nitrogen oxide generation area.

10. The device of claim 7, wherein the predictor is configured to linearize the total nitrogen oxide generation amount of the cylinder to a nitrogen oxide predetermined value.

* * * * *